United States Patent [19]

Wick

[11] Patent Number: Plant 7,209

[45] Date of Patent: Apr. 3, 1990

[54] APPLE TREE: KEYSTONE

[75] Inventor: Randy L. Wick, Riverside, Wash.

[73] Assignee: North American Tree Company, Portland, Oreg.

[21] Appl. No.: 213,317

[22] Filed: Jun. 30, 1988

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Klarquist, Sparkman, Campbell, Leigh & Whinston

[57] ABSTRACT

A new variety of apple tree has a fruit which is a bright yellow color with many fruits taking on a cherry-red blush when exposed to full sunlight; the fruit is generally of a round-conic shape and is less subject to shriveling than Golden Delicious apples when stored; and, my new variety produces high and regular fruit yields.

1 Drawing Sheet

The present invention relates to a new and distinct variety of apple tree which I call "Keystone". I first observed my new variety of apple tree fruiting in a block of Red King Delicious apple trees in about the fall of 1976. This tree was growing in a cultivated area of the Keystone Ranch, an orchard in Riverside, Wash. My new variety of apple tree appeared to have grown from the seedling understock of a mechanically damaged tree. My Keystone cultivar thus appears to be a chance seedling and is of an unknown parentage.

While engaged in the routine care of the orchard, my attention was attracted to my new variety because of the rich golden yellow color of the fruit and because the fruit was shaped more like a Red Delicious apple than a Golden Delicious apple. Close examinations of the parent Keystone apple tree and of its progeny, asexually reproduced at the Keystone Ranch orchard and at other locations by budding and grafting, have convinced me that my new variety is distinguished from all other apple varieties of which I am aware, as evidenced by the following unique combination of characteristics, which have proven firmly fixed, and which are transmitted through succeeding propagation:

(1) Mature fruit which is a bright and rich yellow in color with a distinct cherry-red blush usually showing on fruit exposed to full sunlight;
(2) Fruit which is uniform and attractive in shape, the shape being generally round-conic, somewhat similar to the shape of Red Delicious apples and not as round at the base as Golden Delicious apples;
(3) Fruit which is generally smooth and resistant to russetting, a characteristic of particular importance in areas east of the Rocky Mountains;
(4) Fruit which appears more bruise resistant than Golden Delicious and Criterion apples and with a somewhat waxy surface that makes the fruit less susceptible to shriveling than Golden Delicious apples;
(5) Fruit with a firm flesh and which is excellent for fresh eating and in salads;
(6) Fruit that is especially well adapted to controlled atmosphere (CA) storage;
(7) Fruit that can nearly always be harvested "once over" so that separate pickings for color are seldom required;
(8) Fruit with a distinct and pleasant flavor that seems to be somewhat sweeter in flavor than Golden Delicious apples but more tart in flavor than Red Delicious apples;
(9) Fruit with a pronounced and desirable aroma which makes the fruit useful as an aromatic additive for juice (cider); and
(10) Fruit from the "king" blossoms or clusters, the centermost blossoms of a cluster, which in most years has six or more carpels (locules) instead of the usual five and in which these multiple carpels all seem to merge at the axil of the fruit.

The accompanying illustration shows typical specimens of fruit of my new variety of apple tree, depicted in color as nearly true as is reasonably possible to make the same in a color illustration of this character. In this illustration, certain of the fruit specimens are shown in both elevation and plan views to disclose the exterior details thereof, and other fruit specimens are shown in transverse cross-section to disclose the interior details.

The following comparison chart shows how my new variety of apple tree differs from certain other varieties of apple trees which have generally yellow fruit:

| Variety | Skin | Shape | Bumps | Size | Color |
|---|---|---|---|---|---|
| Criterion | R-0 | Round to Cylind. | P | large | 3 |
| Keystone | R-1 | Round Conic | NP | large | 1 |
| Blushing Golden | R-0 | Round | NP | med large | 1 |
| UltraGold | R-1 | Round | NP | large | 3 |
| Virginia Gold | R-0 | Round Ribbed | NP | large | 2 |
| Starkspur Golden | R-2 | Round | NP | large | 3 |

In the above table, the description of the skin refers to the skin russet, on a scale of from 0 to 5, with 0 being smooth and 5 being full russet. In addition, the term "bumps" in the table refers to the points at the basal end of the fruit with "P" standing for prominent and "NP" standing for not prominent. Also, in the reference to "color" in the table, 1 refers to yellow, 2 refers to white (between yellow and green) and 3 refers to green.

The following is a detailed description of my new Keystone apple tree with color terminology in accordance with The Royal Horticultural Society Colour Chart (hereinafter R.H.S.), published by The Royal Horticultural Society of London, except where ordinary dictionary significance of color is indicated.

Variety: Keystone.

Parentage: Unknown, believed to be a chance seedling.

Locality where described specimens were grown and observed: Keystone Ranch, Riverside, Wash.

Dates of first and last picking: Picked immediately after Red Delicious apples which is usually about October 1st in the Riverside, Wash. area.

Tree:

*Size.*—Medium.

*Vigor.*—Initially strong, medium vigor at maturity.

*Habit.*—Spreading, shorter than Red Delicious trees growing in adjacent areas and which were approximately the same age, round-topped and hardy.

*Fruit production.*—Very productive, sets many spurs very early, in most years the tree has a heavy or satisfactory crop and does not tend to have such a crop only in alternate years as the case of many other varieties.

*Trunk.*—Medium, smooth.

*Branches.*—Medium, smooth, much branching with many fruit spurs, red to brown in color.

Lenticels.—Medium in number, large to medium in size.

*Pollinators.*—Pollinators of my new variety have not yet been fully ascertained, but include Jonathan and are believed to include almost any other variety which issues a viable pollen when my new variety is blooming and receptive to pollination. Whether my new variety is self-fertile has yet to be determined.

Leaves:

*Size.*—Approximately 10 cm. in length and 6 cm in width.

*Shape.*—Oval, abruptly pointed at apex, medium thickness, medium to dark green in color, having a smooth upper surface and a pubescent lower surface.

*Margin.*—Crenate, finely serrate, serrations cant sharply toward apex of leaf.

*Petole.*—Long to medium in length, approximately 3.75 cm. long on the average.

Flowers:

*Flowering period.*—Dates of first and full bloom medium, usually with or one day after Bisbee Red Delicious apples.

*Color.*—Flowers are large and white, pink in the tight bud stage, comparable to Golden Delicious apples.

Fruit:

*Size.*—Uniform, axial diameter typically 8 cm.

*Shape.*—Round, conical, truncate at the base apex.

*Cavity* (*at the stem end*).—Symmetrical, acuminate, pubescent towards apex, depth of 2.2 cm., breadth of 2 cm., smooth golden skin at outer edge of the cavity, but with a russet-like pubescence radiating from the bottom of the cavity.

*Basin* (*at the calyx end*).—Symmetrical, furrowed, glaborous with a light pubesence near calyx, depth typically 1 cm., breadth typically 3 cm.

*Stem.*—Clubbed, slender, 3.5 cm. in length, 3 mm. in breadth, and of a tan color showing a reddish blush on the side exposed directly to sunlight.

*Calyx.*—Segments persistent, erect, reflexed from base at apex, inner and outer surfaces pubescent.

*Eye.*—Medium in size, partially closed.

*Skin.*—Medium tough, smooth, waxed, tan or fawn colored dots are few, large, depressed and conspicuous, some of the dots are areolar, the dots are distributed uniformly in the top two-thirds of the fruit with fewer being located near the calyx end, the skin ground color is bright yellow, like R.H.S. 13-C with a distinct cherry-red blush like R.H.S. 44-A (usually present on fruit exposed to full sunlight), the bloom is wanting and no scarf-skin is present.

*Flesh.*—Rather juicy, comparable to Golden Delicious apples, but not as juicy as Criterion apples, the color of the flesh is satiny white with a yellow tint like R.H.S. 18-D, a texture which is firm and somewhat granular, subacid sweet flavor; pronounced and distinct aroma and a good to best quality fruit.

*Core.*—Sessile — median, — an unequal bundle area with bundles being yellowish, a calyx tube which is pubescent toward base and a style which is distinct toward base, seed cells tender having a length of about 2 cm. and breadth of about 1 cm., seed cells being mucronate in longitudinal section with a tufted surface.

Seeds: Typically up to four medium brown seeds per cell; the seeds are typically 8 mm. long and 4 mm. wide.

Storage: Bruise resistant and easy to store and pack, excellent CA storage, the fruit is of a good keeping quality averaging 180 days in ordinary storage. For example, two bushels of my Keystone variety apples were placed in CA storage in 1987. This fruit was taken out of storage in February 1988 and found to be in excellent condition. Furthermore, this fruit was then held at room temperature for two weeks and still tested at 14 lbs. on a pressure gauge.

Resistance to insects and disease: Good resistance to insects and disease, the tree appears to be resistant to fire blight (*Erwynia amelovora*).

Use: Good for fresh eating, salads, desserts and other culinary uses and for juice.

I claim:

1. A new and distinct variety of apple tree, substantially as herein shown and described, characterized by a fruit with firm flesh, a yellow color which may take on a cherry-red blush when exposed to full sunlight, and which is of a round-conic uniform shape.

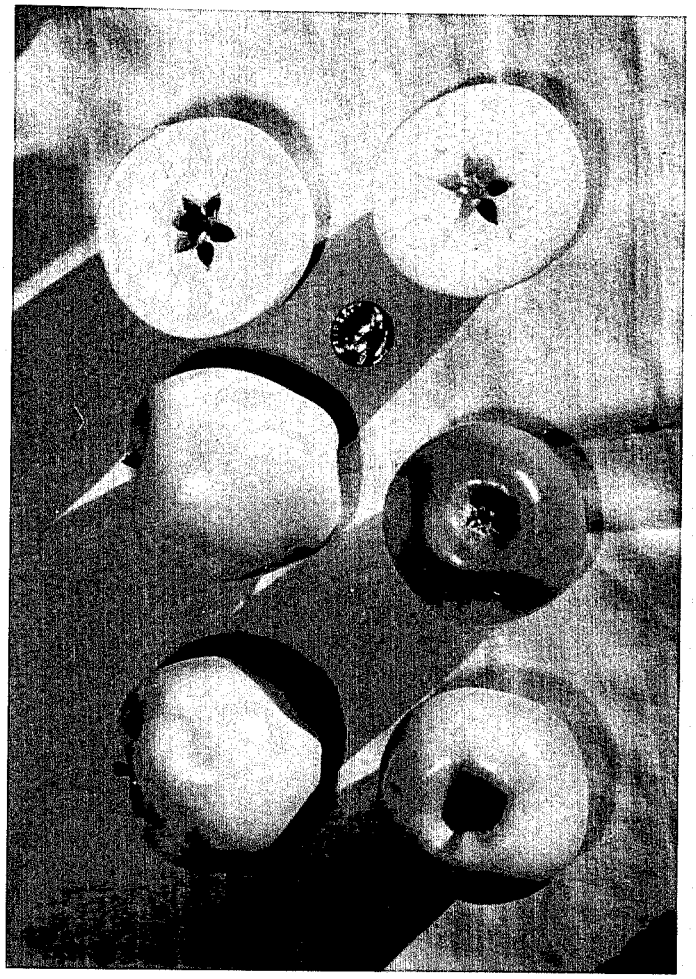

* * * * *